United States Patent
Marks et al.

(10) Patent No.: US 10,227,268 B2
(45) Date of Patent: Mar. 12, 2019

(54) SULFUR AS A SELECTIVE OXIDANT IN OXIDATIVE HYDROCARBON PROCESSING OVER OXIDE/CHALCOGENIDE CATALYSTS

(71) Applicant: Northwestern University, Evanston, IL (US)

(72) Inventors: Tobin J. Marks, Evanston, IL (US); Matthias Peter, Chicago, IL (US)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 15/513,494

(22) PCT Filed: Feb. 19, 2016

(86) PCT No.: PCT/US2016/018756
§ 371 (c)(1),
(2) Date: Mar. 22, 2017

(87) PCT Pub. No.: WO2016/134305
PCT Pub. Date: Aug. 25, 2016

(65) Prior Publication Data
US 2017/0305813 A1 Oct. 26, 2017

Related U.S. Application Data

(60) Provisional application No. 62/176,486, filed on Feb. 19, 2015.

(51) Int. Cl.
*C07C 2/84* (2006.01)
*B01J 27/04* (2006.01)
(Continued)

(52) U.S. Cl.
CPC ............... *C07C 2/84* (2013.01); *B01J 27/04* (2013.01); *B01J 27/043* (2013.01); *B01J 35/023* (2013.01);
(Continued)

(58) Field of Classification Search
CPC .... C07C 2/84; B01J 37/20; B01J 37/43; B01J 27/04; B01J 21/063; B01J 21/066;
(Continued)

(56) References Cited

U.S. PATENT DOCUMENTS 4,620,057 A * 10/1986 Kimble ............... B01J 27/1853
585/415
5,068,486 A 11/1991 Han et al.
(Continued)

FOREIGN PATENT DOCUMENTS

EP 0210383 2/1987

OTHER PUBLICATIONS

Zhu, Q. et. al. "Sulfur as a selective 'soft' oxidant for catalytic methane conversion probed by experiment and theory", Nat. Chem., 5 (2012); pp. 104-109 and Supplementary Information, pp. 1-35). (Year: 2012).*

(Continued)

*Primary Examiner* — Philip Y Louie
*Assistant Examiner* — Aaron W Pierpont
(74) *Attorney, Agent, or Firm* — Bell & Manning, LLC (57) ABSTRACT

Methods for oxidative coupling of methane using metal oxide catalysts and a sulfur oxidant.

20 Claims, 10 Drawing Sheets

(51) Int. Cl.

| | | |
|---|---|---|
| *B01J 27/043* | (2006.01) | |
| *B01J 35/02* | (2006.01) | |
| *B01J 37/20* | (2006.01) | |
| B01J 21/06 | (2006.01) | |
| B01J 23/06 | (2006.01) | |
| B01J 23/745 | (2006.01) | |
| B01J 21/10 | (2006.01) | |
| B01J 23/10 | (2006.01) | |
| B01J 23/24 | (2006.01) | |
| B01J 35/00 | (2006.01) | |
| B01J 35/10 | (2006.01) | |

(52) U.S. Cl.
CPC ............ *B01J 37/20* (2013.01); *B01J 21/06* (2013.01); *B01J 21/10* (2013.01); *B01J 23/06* (2013.01); *B01J 23/10* (2013.01); *B01J 23/24* (2013.01); *B01J 23/745* (2013.01); *B01J 35/002* (2013.01); *B01J 35/0013* (2013.01); *B01J 35/1009* (2013.01); *B01J 35/1014* (2013.01); *C07C 2521/06* (2013.01); *C07C 2521/10* (2013.01); *C07C 2523/06* (2013.01); *C07C 2523/10* (2013.01); *C07C 2523/26* (2013.01); *C07C 2523/30* (2013.01); *C07C 2523/745* (2013.01); *C07C 2527/04* (2013.01); *C07C 2527/043* (2013.01); *C07C 2527/047* (2013.01); *C07C 2527/051* (2013.01); *Y02P 20/52* (2015.11)

(58) Field of Classification Search
CPC ... B01J 21/10; B01J 23/06; B01J 23/10; B01J 23/26; B01J 23/30; B01J 23/74; B01J 27/047
USPC ........................................................ 585/500
See application file for complete search history.

(56) References Cited

U.S. PATENT DOCUMENTS

| 5,191,138 A * | 3/1993 | Han .................... C07C 2/82 585/415 |
|---|---|---|
| 5,321,185 A * | 6/1994 | van der Vaart .......... C07C 2/84 585/500 |
| 2006/0207917 A1* | 9/2006 | Domokos ............. B01J 29/076 208/120.1 |
| 2014/0200383 A1* | 7/2014 | Marks ..................... C07C 2/84 585/658 |

OTHER PUBLICATIONS

Anderson, J. R. et. al. "Reaction of Methane and Sulfur: Oxidative Coupling and Carbon Disulfide Formation", React. Kinet. Catal. Lett., vol. 49, No. 2 (1993); pp. 261-269. (Year: 1993).*

Meyer, B. "Elemental Sulfur", Chem. Rev., 76, (1976); pp. 367-388 (Year: 1976).*

Moreau, P. et al., "Electronic Structures and Charge Transfer in Lithium and Mercury Intercalated Titanium Disulfides", J. Phys. Chem. Solids, 1996, 57, 1117-1122.

Gonbeau, D. et al., "XPS study of thin films of titanium oxysulfides", Surf. Sci., 1991, 254, 81-89.

Franzen, H. F. et al., "XPS Spectra of Some Transition Metal and Alkaline Earth Monochalcogenides" J. Solid State Chem., 1976, 18, 363-368.

Hernan, L. et al., "Diffraction and XPS Studies of Misfit Layer Chalcogenides Intercalated with Cobaltocene", Chem. Mater., 1995, 7, 1576-1582.

Baltrusaitis, J. et al., "Sulfur Dioxide Adsorption on TiO2 Nanoparticles: Influence of Particle Size, Coadsorbates, Sample Pretreatment, and Light on Surface Speciation and Surface Coverage", J. Phys. Chem. C 2011, 115, 492-500.

Pratt, A. R. et al., "X-ray photoelectron and Auger electron spectroscopic studies of pyrrhotite and mechanism of air oxidation", Geochim. Cosmochim. Acta, 1993, 58, 827-841.

Nesbitt, H. W. et al., "Sulfur and iron surface states on fractured pyrite surfaces", Am. Mineral. 1998, 83, 1067-1076.

Zhu, Q. et al., "Sulfur as a selective 'soft' oxidant for catalytic methane conversion probed by experiment and theory", Nat Chem 2012, 5 (2), 104-109.

Karan, K. et al., "CS2 Formation in the Claus Reaction Furnace: A Kinetic Study of Methane-Sulfur and Methane Hydrogen Sulfide Reactions", Ind. Eng. Chem. Res., 43, 3300-3313, 2004.

Didenko, L.P. et al., "Partial catalytic oxidation and condensation of methane by oxygen and sulphur", Catal. Today 1998, 42, 367-370.

Anderson, J.P. et al., "Reaction of Methane and Sulfur: Oxidative Coupling and Carbon Disulfide Formation", React. Kinet. Catal. Lett. 1993, 49, 261-269.

Extended European Search Report mailed in European Application No. 16753181.3, dated Sep. 11, 2018.

Horn et al., Methane Activation by Heterogeneous Catalysis, CATAL. LETT., vol. 145, No. 1, Nov. 20, 2014, pp. 23-39.

Naito, Methane conversion by various metal, metal oxide and metal carbide catalysts, Catalysis Surveys from Japan, (2000), vol. 4, pp. 3-15.

* cited by examiner

SULFUR AS A SELECTIVE OXIDANT IN OXIDATIVE HYDROCARBON PROCESSING OVER OXIDE/CHALCOGENIDE CATALYSTS

This application claims priority to and the benefit of International Application no. PCT/US2016/018756 filed Feb. 19, 2016, which claimed priority to and the benefit of application Ser. No. 62/176,486 filed Feb. 19, 2015—each of which is incorporated herein by reference in its entirety.

BACKGROUND OF THE INVENTION

Figure 1:
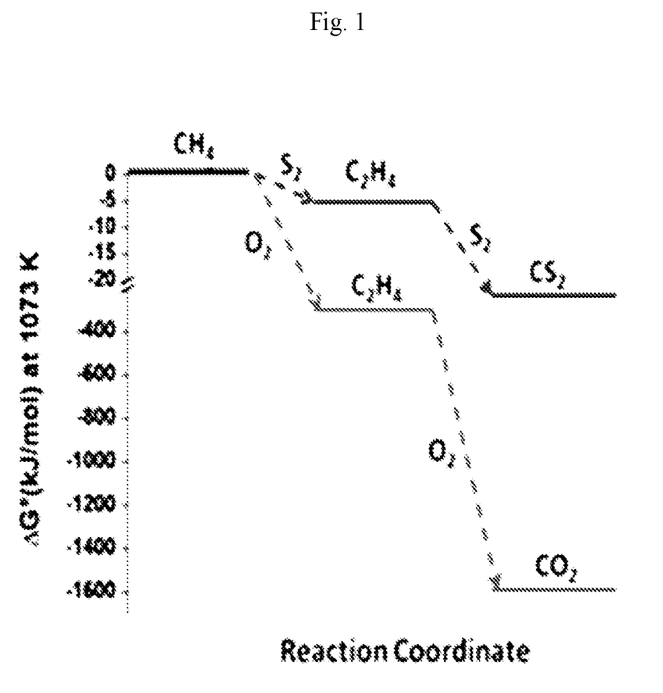
FIG. 1. Comparison of the free energies of the principal species involved in the oxidative coupling of $CH_4$ by $S_2$ (upper plot) and $O_2$ (lower plot).

The increasing demand for ethylene as a chemical feedstock along with the limited availability of petroleum reserves and the emergence of shale gas production have fueled renewed interest in developing direct and efficient catalytic sequences for the oxidative coupling of methane (OCM) to ethylene. Numerous studies have focused on OCM with $O_2$ as the oxidant to optimize the $C_2$ yield and to elucidate the reaction mechanism. Alkaline earth oxides, early transition metal oxides, and rare earth oxides are found to be promising catalysts, and enhanced catalytic performance can be achieved by adding dopants and/or promoters. Nevertheless, large scale applications of OCM with $O_2$ have yet to be implemented, primarily attributable to the large thermodynamic driving force for over-oxidation (FIG. 1), which compromises $C_2$ selectivity, and the difficulty of reactor engineering for such highly exothermic processes. Other approaches for converting $CH_4$ to valuable feedstocks such as the non-oxidative coupling of $CH_4$ have attractions but also significant limitations, and to date have not seen large-scale use.

An alternative to the above approaches seeks to moderate the driving force for methane over-oxidation by employing a "soft" oxidant such as $S_2$ (SOMC). Note that the $\Delta G$ for $CH_4$ over-oxidation by $S_2$ is -236 kJ/mol versus -1294 kJ/mol for $O_2$ (FIG. 1), suggesting that higher ethylene selectivities/yields might be possible using less aggressive 'soft' oxidants along with an optimum catalyst. The lower SOCM exothermicity versus that with $O_2$ might also offer advantages in reactor design, and the $H_2S$ co-product could be efficiently reconverted to sulfur via the Claus process. In earlier work it was envisioned that the optimum catalysts for creating S—C bonds along plausible sulfur-based OCM reaction coordinates might be those which cleave S—C bonds and are not poisoned by large quantities of $S_2$, such as hydrodesulfurization catalysts.

Accordingly, a series of transition metal chalcogenides (e.g., $TiS_2$, $RuS_2$, $MoS_2$, PdS, etc.) was investigated for SOCM in a specialized reactor, affording $CH_4$ conversions and $C_2H_4$ selectivities at 950° C. of 6-9% and 4-9%, respectively. In conjunction with these experimental studies, computational investigations showed that the M-S bond strength has a major influence on the $CH_4$ conversion and the $C_2H_4$ selectivity, the two of which are inversely related. However, issues remain in the art as to the role of the transition metal and the particular oxide support in this catalytic transformation, and as to whether there are alternatives to such a noble metal catalyst system—to better realize the benefits and advantages available through use of a $S_2$ oxidant.

SUMMARY OF THE INVENTION

In light of the foregoing, it is an object of the present invention to provide a system for the oxidative coupling of methane by gaseous sulfur and various metal oxide/chalcogenide catalysts which can be used therewith, thereby overcoming various deficiencies and shortcomings of the prior art, including those outlined above.

It can be an object of the present invention to provide a thermo-dynamically moderate reaction system for the oxidative coupling of methane.

It can also be an object of the present invention to provide a non-transition/noble metal catalyst useful in conjunction with a gaseous sulfur oxidant for the oxidative coupling of methane.

It can also be an object of the present invention, alone or in conjunction with one or more of the preceding objectives, to provide a method for selective production of ethylene over ethane and acetylene.

Other objects, futures, benefits and advantages of the present invention will be apparent from this summary and the following descriptions of certain embodiments, and will be readily apparent to those skilled in the art having knowledge of catalytic systems for the oxidative coupling of methane. Such objects, futures, benefits and advantages will be apparent from the above as taken into conjunction with the accompanying examples, data, figures and all reasonable inferences to be drawn therefrom.

In part, the present invention can be directed to a method for oxidatively coupling methane. Such a method can comprise providing a metal oxide component; exposing such a metal oxide component to gaseous sulfur for at least one of a time and a temperature sufficient for at least partial sulfidation or sulfide conversion of such a metal oxide component; and contacting such a sulfidated or converted component with methane for at least one of a methane flow rate and a time sufficient to oxidatively couple methane and produce ethylene. Representative metal oxide components useful in conjunction with the present methodology are described below. Various other metal oxide/chalcogenide components can also be considered, as would be understood by those skilled in the art and made aware of this invention, such oxide/chalcogenide components limited only by functional capacity to catalyze the oxidative coupling of methane to ethylene using S2 as an oxidant.

More specifically, such a method can comprise providing a metal oxide component selected from MgO, $ZrO_2$, $TiO_2$, $CeO_2$, $Sm_2O_3$, ZnO, $WO_3$, $Cr_2O_3$, $La_2O_3$, and $Fe_3O_4$; exposing such a metal oxide component to gaseous sulfur for at least one of a time and a temperature sufficient for at least partial sulfidation or sulfide conversion of such a metal oxide component; and contacting such a sulfidated or converted component with methane for at least one of a methane flow rate and a time sufficient to oxidatively couple methane and selectively produce ethylene over ethane and acetylene.

In part, the present invention can also be directed to a method of using a metal oxide to catalyze oxidative coupling of methane. Such a method can comprise providing a metal oxide catalyst component selected from MgO, $ZrO_2$, $TiO_2$, $CeO_2$, $Sm_2O_3$, ZnO, $WO_3$, $Cr_2O_3$, $La_2O_3$, and $Fe_3O_4$, such a catalyst component absent the presence of a noble metal; exposing such a metal oxide catalyst component to gaseous sulfur for at least one of a time and a temperature sufficient for at least partial sulfidation or sulfide conversion of such a metal oxide catalyst component; and contacting such a sulfidated or converted component with methane for at least one of a methane flow rate and a time sufficient to oxidatively couple methane and produce ethylene.

DETAILED DESCRIPTION OF CERTAIN EMBODIMENTS

Certain non-limiting embodiments of this invention were employed to illustrate use of neat metal oxides for SOMC, to address one or more of the preceding objectives. As demonstrated, significant ethylene yields and selectivities are achieved over certain metal oxides which exceed those achieved with supported Pd, a metal representative of the prior art.

The catalytic measurements were conducted in the flow bed reactor described previously, designed to use gaseous $S_2$ as the hydrocarbon oxidant. (See, e.g., (a) Moreau, P.; Ouvrard, G.; Gressier, P.; Ganal, P.; Rouxel, J., *J. Phys. Chem. Solids* 1996, 57, 1117; (b) Gonbeau, D.; Guimon, C.; P-Guillouzo, G.; Levasseur, A.; Meunier, G.; Dormoy, R., *Surf Sci.* 1991, 254, 81-89; (c) Franzen, H. F.; Umana, M. X.; McCreary, J. R.; Thorn, R. J., *J. Solid State Chem.* 1976, 18, 363; (d) Hernan, L.; Morales, J.; Sanches, L.; Tirado, J. L.; Espinos, J. P., *Chem. Mater.* 1995, 7, 1576; (e) Baltrusaitis, J.; Jayaweera, P. M.; Grassian, V. H., *J. Phys. Chem. C* 2011, 115, 492-500; (f) Pratt, A. R.; Muir, J. J.; Nesbitt, H. W., *Geochim. Cosmochim. Acta* 1993, 58, 827-841; and (g) Nesbitt, H. W.; Bancroft, G. M.; Pratt, A. R.; Scaini, M. J., *Am. Mineral.* 1998, 83, 1067-1076.) Catalytic experiments were performed using, without limitation, a mixture of 2.7% $CH_4$ in Argon and a $CH_4/S$ ratio of 7.5, with 0.06% $H_2S$ added to diminish coking. After heating the catalysts in the absence of $CH_4$ to 950° C., these "precatalysts" were exposed to $S_2$ for 4 hours at 950° C. Subsequently, the catalysts were exposed to the reactant mixture for at least 16 hours at 950° C., and the effluent distribution was monitored continuously by gas chromatography.

In order to discuss the catalytic results together with the structural and compositional evolution of the oxides during the reaction, the latter is considered first. Before reaction with the $CH_4/S_2/Ar$ mixture, the oxides are in the form of nanopowders with surface areas of ≥10 m$^2$/g (except for $WO_3$, area=9.3 m$^2$/g). Note that the catalyst surface area is significantly reduced after SOCM at 950° C. (Table 1), similar to previous observations for OCM with $O_2$. For half of the oxides, the surface areas after reaction are less than 0.5 m$^2$/g.

TABLE 1

Structural properties of catalysts after reaction under catalytic conditions at 950° C. for 16 hours.

|  | Phases Detected by XRD | Sulfur* | Carbon* | Surface Area* |
|---|---|---|---|---|
| MgO | MgS, MgO, | 46.44% | 8.05% | 9.47 |
| $ZrO_2$ | $ZrO_2$, $ZrS_2$ | 9.74% | 6.16% | 6.29 |
| $TiO_2$ | $TiO_2$, $Ti_3S_4$ | 3.72% | <0.5% | 0.42 |
| $CeO_2$ | $Ce_{10}S_{14}O$, $Ce_4S_3O$ | 4.11% | <0.5% | 0.46 |
| $Sm_2O_3$ | $Sm_{10}S_{14}O$, $Sm_2O_2S$ | 17.51% | 0.56% | 0.18 |
| $Fe_3O_4$ | $FeS_2$, FeS, $Fe_{1-x}S$ | 36.84% | <0.5% | 0.07 |
| ZnO | ZnS, ZnO | 31.95% | <0.5% | 0.22 |
| $WO_3$ | $WS_2$ | 22.11% | 6.77% | 1.88 |
| $La_2O_3$ | $La_{10}S_{14}O_{0.5}$ | 23.70% | 2.00% | 1.89 |
| $Cr_2O_3$ | $Cr_{1.89}S_3$, $Cr_2S_3$ | 41.22% | <0.5% | 0.67 |

*S and C content by combustion analysis, BET surface area in m$^2$/g

In general, metal sulfides, oxides and oxysulfides are detected in the spent catalysts by XRD (Table 1). The extent of oxide to sulfide (i.e., the degree of) conversion is strongly oxide dependent: the intensity of the Bragg peaks and the S content indicate that MgO is largely converted into MgS whereas only a small fraction of $TiO_2$ and $ZrO_2$ are converted to a sulfide (e.g., a partial conversion). On $CeO_2$ and $Sm_2O_3$, oxysulfides are identified with the lower intensity/width of the diffraction peaks indicating that the catalysts are amorphous to a significant degree, which is also the case for the $Fe_3O_4$ catalyst after reaction. Combustion analysis and UV Raman spectroscopy also reveal that significant amounts of coke as a mixture of graphite and defective/amorphous carbon is deposited by SOCM at 950° C. on MgO, $ZrO_2$, $WO_3$, $La_2O_3$ and $Sm_2O_3$. XPS was also employed to investigate changes in surface composition during SOCM. After 30 s sputtering with 3 keV $Ar^+$ ions, the C 1s spectra show a surface C coverage >80% on the Mg-, Zr-, W-, La- and Sm-chalcogenides, and ≤15% on the Ti-, Cr- and Fe-based catalysts, respectively. The surface C coverage of the Ce and Zn catalysts after SOCM is ~68% and ~36%, respectively. (Note that this extent of coking was not observed previously for Pd-based SOCM catalysts.)

In addition to a lower surface C content, the spent Ti, Zn, Cr and Fe catalysts also differ from the other catalysts in the nature of the O surface species. On the Ti and Fe chalcogenides, XPS O 1s features at ~530 eV evidence the presence of metal oxides, whereas negligible or only very weak features at 530 eV-531 eV are observed on the Mg, Ce, Sm and Zr catalysts. For both of these types of chalcogenides, S 2p transitions at 161 eV-162 eV confirm the presence of metal sulfides. The spent Sm, Ce, W, Zr and Mg catalysts, which contain considerable amounts of surface coke also exhibit a single peak at ~532 eV and a doublet at ~164 eV, which both do not decrease significantly upon 30 s $Ar^+$ sputtering. These features indicate the presence of C—O—C and C—S—C or $S_n$ species.

Figure 2A:
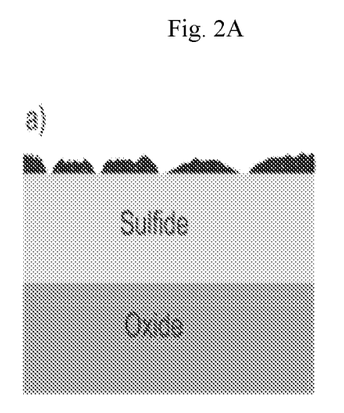
FIGS. 2A-B. Schematic representation of the two different types of sulfides formed during SOCM at 950° C.
Figure 2B:
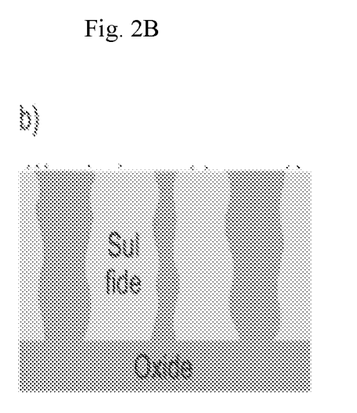
Figure 3A:
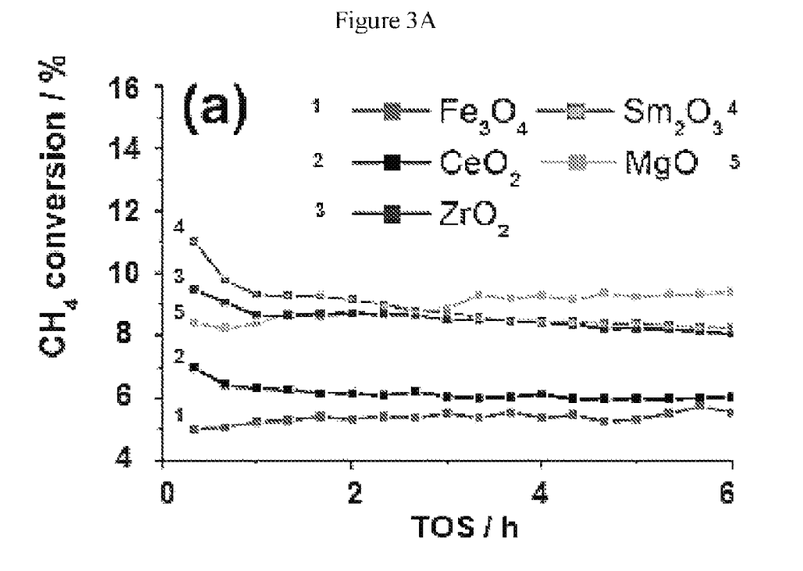
FIGS. 3A-D. $CH_4$ conversion (A), (B) and $C_2H_4$ selectivity (C), (D) plotted vs SOCM time-on-stream (TOS) at 950° C. with a contact time of 1.33 mg·min/mL and a $CH_4/S$ ratio of 7.5.
Figure 3B:
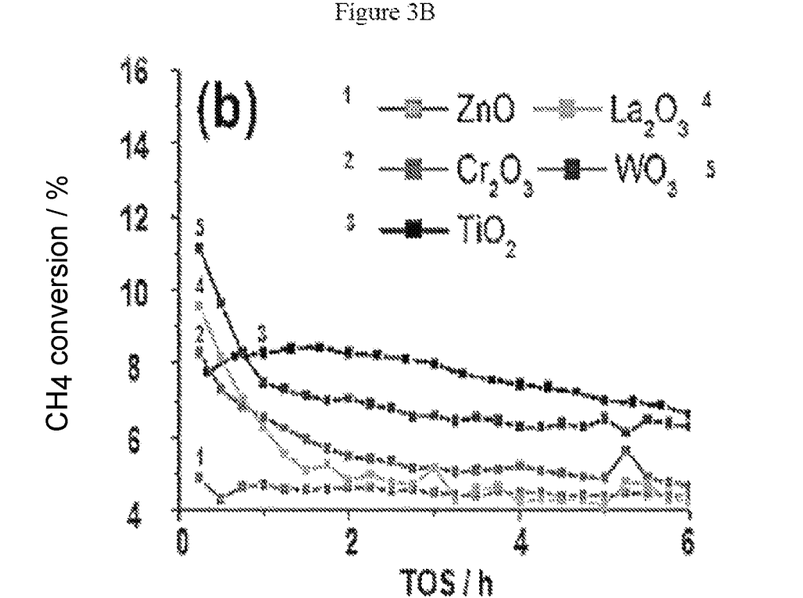
Figure 3C:
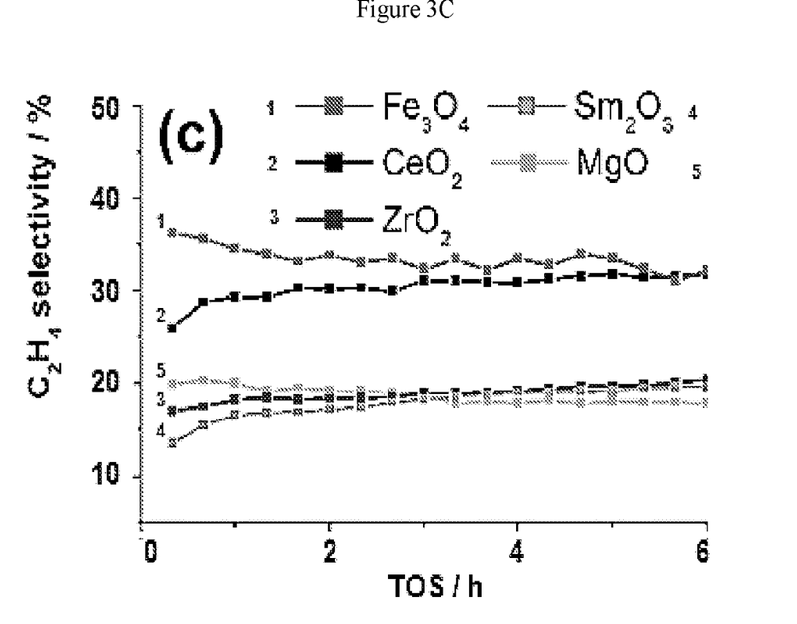
Figure 3D:
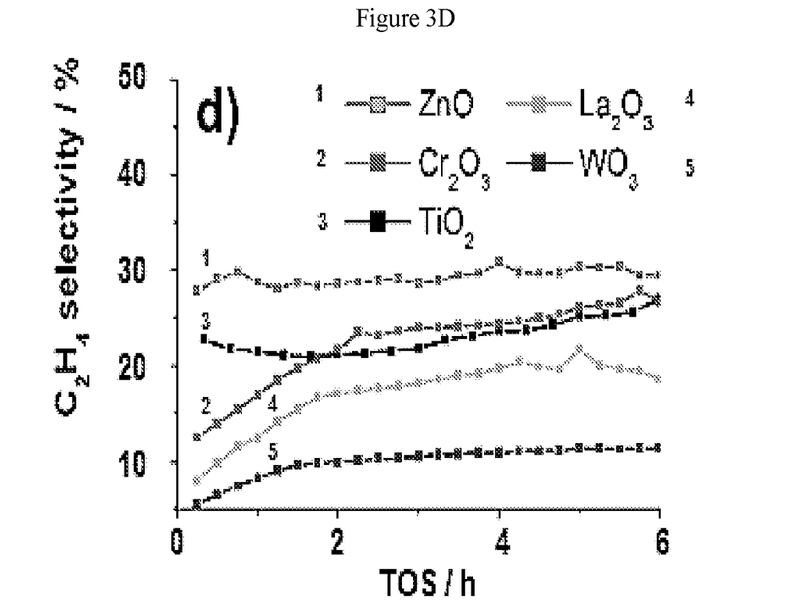

FIG. 2 shows a tentative model for the two different types of chalcogenides. On all catalysts, a mixture of oxides and sulfides is present after SOCM. On Type A catalysts, MgO, $CeO_2$, $Sm_2O_3$, $WO_3$, $La_2O_3$ and $ZrO_2$, after reaction, significant amounts of coke containing O and S are found. Beneath the coke layer, a metal sulfide is formed during SOCM. (FIG. 2A) On type B catalysts, Ti-, Fe-, Zn- and Cr-based catalysts, only minor amounts of surface C are present in addition to both oxides and sulfides. (FIG. 2B) Based on earlier studies of other reaction systems in which coke is formed during the catalytic process, deactivation of the Mg, Zr, and Sm catalysts might be expected during SOCM.

Catalytic SOCM studies were carried out under the conditions, indicated above. After 6 hours with a contact time of 1.33 min mg/mL, the flow rate was adjusted to a contact time of 1.67 min mg/mL, and after 5 hours, the contact time was further increased to 2.22 min mg/mL for 5 hours. The reactivity data reported here were obtained as the average of at least three independent measurements. The reaction products $C_2H_4$, $C_2H_6$, $C_2H_2$, and $CS_2$ were identified, with the selectivity for mercaptans far below 1%. Depending on the catalyst, the $C_2H_4/C_2H_6$ ratio is in the range 8.9-12.4, with the $C_2H_4/C_2H_2$ ratio in the range 7.3-16.6 for the larger contact time of 2.22 mg·min/mL. Accordingly, the target molecule $C_2H_4$ is by far the most abundant $C_2$ product, in contrast to reports for typical OCM with $O_2$.

For SOCM at a contact time of 1.33 mg min/mL, $CH_4$ conversion over all ten catalysts ranges between 4% and 11% and $C_2H_4$ selectivity, 5%-35% (FIG. 3). At 950° C., SOCM over the noble metal sulfides, studied earlier achieved similar conversions but $C_2H_4$ selectivities were less than half. Clearly, noble metals are not necessary for high SOCM selectivity. After an induction time of ~1 hour, variations in $CH_4$ conversion (FIG. 3A) and $C_2H_4$ selectivity (FIG. 3B) are not significant over 5 hours for the Ce-, Fe-, Zn-, Mg-, and Zr-chalcogenide catalysts, whereas larger variations are observed for the Ti-, W-, Cr- and Sm-based counterparts. The $C_2H_4$ yield increases with contact time: it is on average higher by 5% and 6% if the contact time is increased from 1.33 mg min/mL to 1.67 mg min/mL and 2.22 mg min/mL, respectively.

Note that the Mg and Zr chalcogenides, which form substantial C deposits during SOCM, exhibit stable catalytic properties. Thus, coking does not lead to gradual catalyst deactivation as is frequently the case in other catalytic systems. Even after increasing the contact time from 1.33 mg min/mL to 1.67 mg min/mL, and 5 hours later to 2.22 mg min/mL, no consistent decreases of the $CH_4$ conversion are observed over the Sm, Mg, and Ce catalysts which form considerable amounts of coke. Accordingly, coking does not lead to deactivation in these cases. Since $CH_4$ diffusion on the surfaces before reaction should be negligible, it is concluded that $CH_4$ is readily activated on the coked surfaces. In contrast to $CH_4$ conversion, the average $C_2H_4$ yields for the highest performing Fe- and Ce-based catalysts are 10% greater than for the other catalysts using a 2.22 mg min/mL contact time. On both of these oxides, smaller amounts of C deposits are formed than on the Mg, Zr and Sm catalysts, suggesting that some degree of coking resistance is necessary to achieve the highest $C_2H_4$ yields.

Figure 4:
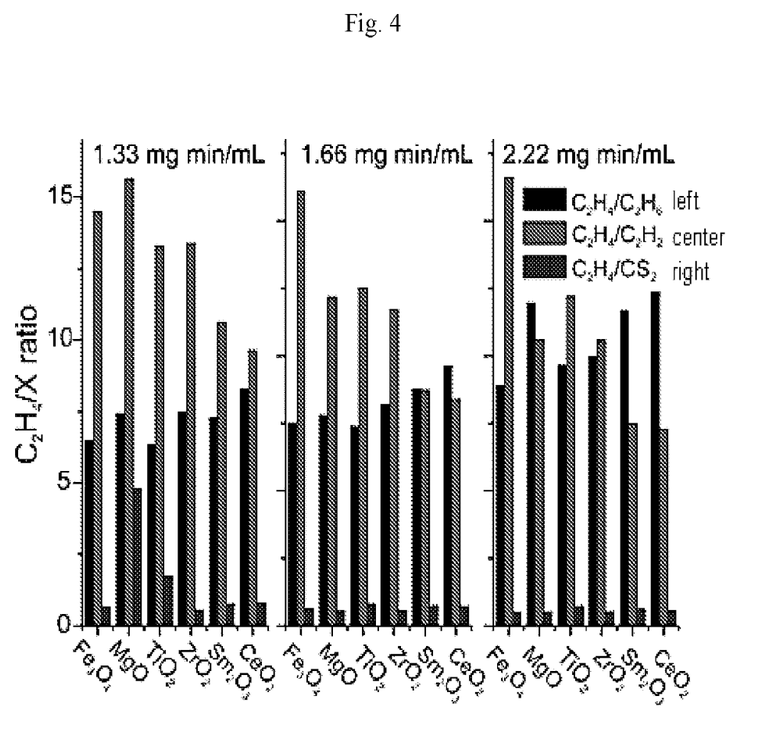
FIG. 4. Contact time dependence of the average $C_2H_4/C_2H_6$ ratio (left bar), the $C_2H_4/C_2H_2$ ratio (center bar) and the $C_2H_4/CS_2$ ratio (right bar) for SOCM over the present catalysts.

Regarding the SOMC reaction pathways for $C_2H_4$ and $C_2H_2$ formation, the average $C_2H_4/C_2H_6$ and $C_2H_4/C_2H_2$ ratios for the three different contact times are compared in FIG. 4 for six catalysts. With increasing contact time, the $C_2H_4/C_2H_6$ ratio clearly increases while the $C_2H_4/C_2H_2$ ratio falls, which suggests that the relative selectivity to $C_2H_6$ falls while the relative selectivity to $C_2H_2$ increases with reaction time. Without limitation to anyone theory, mode of operation or mechanism, these findings provide strong evidence that to a significant extent over the present catalysts, $C_2H_4$ and $C_2H_2$ are formed via the dehydrogenation of $C_2H_6$ and $C_2H_4$, respectively. FIG. 4 also shows that the relative $C_2H_2$ selectivity is lowest for the Fe- and Ti-based catalysts, both of which do not form large quantities of coke. In contrast, the relative $CS_2$ selectivity is highest for the Ti and lowest for Fe-based catalysts, suggesting that coke is likely formed from acetylene and not from $CS_2$, in accord with studies of other catalytic systems where coke is formed from unsaturated hydrocarbons.

EXAMPLES OF THE INVENTION

The following non-limiting examples and data illustrate various aspects and features relating to the methods and/or catalysts of the present invention, including the selective oxidative coupling of methane to ethylene, as is available through the methodologies described herein. In comparison with the prior art, the present methods and catalysts components provide results and data which are surprising, unexpected and contrary thereto. While the utility of this invention is illustrated through the use of representative metal oxide components which can be used therewith, it will be understood by those skilled in the art that comparable results are obtainable with various other metal oxide/chalcogenide components, as are commensurate with the scope of this invention.

Reactor Measurements

1. Experimental Setup. Detailed information on the experimental setup is as provided in the literature. (See, e.g., Zhu, Q.; Wegener, S. L.; Xie, C.; Uche, O.; Neurock, M.; Marks, T. J., *Nat Chem* 2012, 5 (2), 104-109.) Briefly, the reactor is situated in an oven which contains a sulfur vapor generator, a preheat furnace and a reactor furnace. Elemental sulfur is generated by heating the oven to a temperature of 470 K and passing a constant 40 ml/min Argon stream through the sulfur vapour generator. To convert $S_x$ into $S_2$, the preheat furnace is set to a temperature of 923 K. Subsequently, $CH_4$ and a trace of $H_2S$ is added to the $S_2$/Ar effluent, and the educt mixture is directed through the reactor furnace containing 200 mg of catalyst. After exiting the reactor region, the product stream is directed through an $S_2$ condenser to trap unreacted sulfur and the products are analysed with GC (Agilent 7890 GC).

2. Experimental Procedure. The ten, representative oxide nanopowders, used in the current experiments, were purchased from Sigma Aldrich, Strem Chemicals or Alfa Aesar and exhibit a purity of ≥99.95%. According to the manufacturers specification, the surface areas of $ZrO_2$, $TiO_2$, $Sm_2O_3$, $CeO_2$, $Fe_3O_4$ and MgO are >25 m$^2$/g, 130-190 m$^2$/g, <10 m$^2$/g, 30 m$^2$/g, 60 m$^2$/g and 200 m$^2$/g, respectively. After pressing the oxides into pellets and grinding, particles with a diameter of 180 μm-300 μm were extracted and filled into the reactor tube.

The educts consist of 2.7% $CH_4$ in Argon and a $CH_4$/S ratio of 7.5 and 0.06% $H_2S$. After calibration of the $CH_4$ flow, the oven, preheat furnace and reactor furnace were set to their respective desired temperatures in a flow of $S_2/H_2S$/ Ar. After 4 hours at the reaction temperature, $CH_4$ was introduced with an effluent flow rate of 150 ml/min (contact time 1.33 mg·min/ml) for 6 hours. Subsequently, the flow rate was increased to 120 ml/min (contact time 1.67 mg·min/ ml) and after 5 hours further to 150 ml/min (contact time 2.22 mg·min/ml). By using Argon as a balance gas, the educt concentrations were held constant.

3. $C_2H_4$ yield as a function of the contact time. In Table 2, the $C_2H_4$ yield is shown for the three contact times, used in our experimental procedure.

TABLE 2

C$_2$H$_4$ yield measured after 5 hours on stream at 950° C. in a CH$_4$/S$_2$/Ar mixture and a CH$_4$/S ratio of 7.5 at three different contact times.

| t$_{contact}$ | 2.22 mg · min/mL | 1.67 mg · min/mL | 1.33 mg · min/mL |
|---|---|---|---|
| Fe$_3$O$_4$ | 2.17 | 1.93 | 1.77 |
| MgO | 1.89 | 1.75 | 1.67 |
| TiO$_2$ | 1.93 | 1.83 | 1.77 |
| ZrO$_2$ | 1.98 | 1.80 | 1.63 |
| Sm$_2$O$_3$ | 2.08 | 1.91 | 1.78 |
| CeO$_2$ | 2.15 | 2.00 | 1.91 |

The C$_2$H$_4$ yield increases with contact time: it is higher by 5% and 6% if the contact time increases from 1.33 mg min/ml to 1.67 mg min/ml and 2.22 mg min/ml, respectively. It is evident that the C$_2$H$_4$ yield is strongly enhanced for the Fe and Ce catalysts. For the contact time 2.22 mg·min/ml, the C$_2$H$_4$ yield for these two catalysts is on the average 10% higher than for the other ones. This suggests that catalysts should exhibit some degree of coking resistance in order to give high C$_2$H$_4$ yields. Interestingly TiO$_2$ shows relatively low C$_2$H$_4$ yields although only minor coking occurs on TiO$_2$.

Figure 5A:
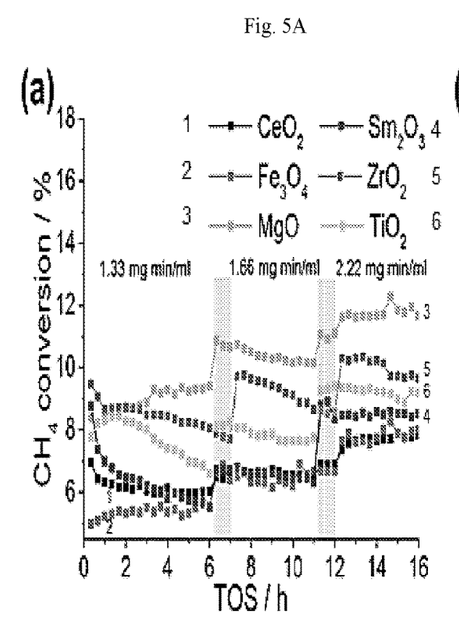
FIGS. 5A-B. $CH_4$ conversion (A) and $C_2H_4$ selectivity (B) plotted vs SOCM time on stream (TOS) at 950° C. with a contact time of 1.33 mg·min/mL, 1.66 mg min/ml and 2.22 mg min/ml. A $CH_4/S$ ratio of 11.9 was maintained.
Figure 5B:
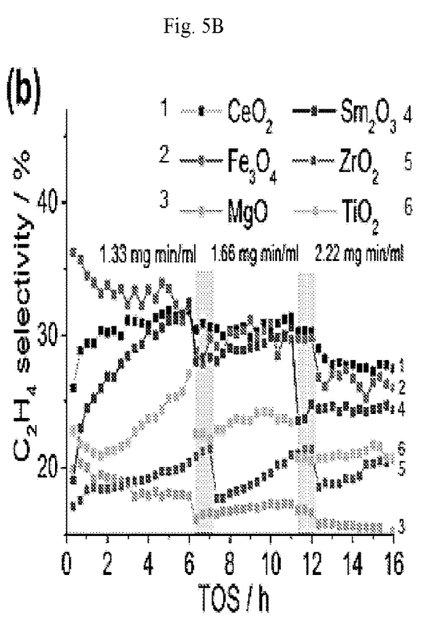

FIGS. 5A and 5B show the CH$_4$ conversion and the C$_2$H$_4$ selectivity versus the time on stream for all three contact times, all shown data were obtained as the average of at least 3 independent measurements. Note that in the case of ZrO$_2$, the contact time was increased after 7 hours and 12 hours from 1.33 mg min/ml to 1.66 mg min/ml and 2.22 mg min/ml. For the other catalysts, the contact times were already changed after 6 and 11 hours.

Spectroscopic Studies

1. X-Ray Diffraction. In order to clarify the structural changes of the different catalysts under SOMC reaction conditions, XRD data from the catalysts after the reaction at 950° C. were collected using a Rigaku (Rigaku Ultima IV) powder X-ray diffractometer with Cu Kα radiation and a Ni filter. The XRD instrument was operated at 40 kV and 20 mA. The step size was set to 0.05° with a count time of 2 s per step. The background subtracted XRD spectra (not shown), taken on the 6 different samples after reaction at 950° C. in the CH$_4$/S$_2$/Ar mixture with a trace of H$_2$S, indicate multiple phases generally coexist.

Figure 6:
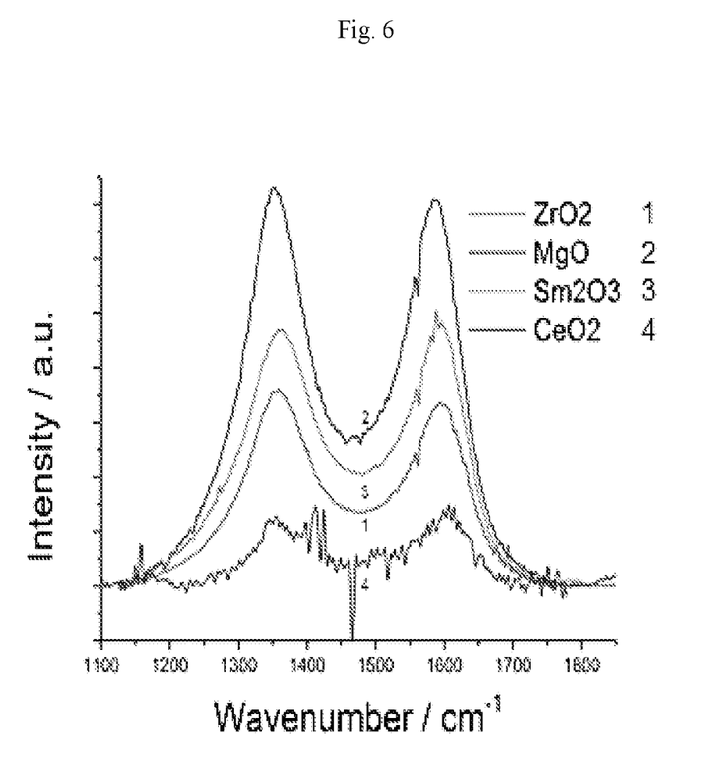
FIG. 6. Raman spectra of the different catalysts after exposure to a $CH_4/S_2$ mixture at 950° C. for 16 hours. No features were detected in this spectral range on the Fe and Ti catalysts.

2. Raman Spectroscopy. Raman spectroscopy was performed on the catalysts after reaction at 950° C. under the conditions, described above (Acton TriVista CRS). All spectra were recorded using 514.5 nm radiation, a Laser power of 0.2 mW and a data collection time of 5 min. FIG. 6 shows the Raman spectra for Zr, Mg, Sm and Ce catalysts after reaction in the range 1100-1850 cm$^{-1}$. No features were observed in this region for Ti and Fe catalysts. The band at ≈1600 cm$^{-1}$ is associated with phonon modes in the graphene structure. Accordingly, this mode is indicative of crystalline graphite. The band at 1350 cm$^{-1}$ has previously been associated with defective and disordered carbon structures, carbon nanoparticles, amorphous carbon or defective filamentous carbon. Both modes are observed for the chalcogenides of Zr, Mg, Sm and Ce, which shows that C is present in both forms. That the signal intensity is very weak for the Ce compound and no features can be observed at 1350 cm$^{-1}$ and 1580 cm$^{-1}$ for Ti and Fe catalysts is in agreement with the XPS data in which it was found that significantly less C is present on these three oxides.

Figure 7A:
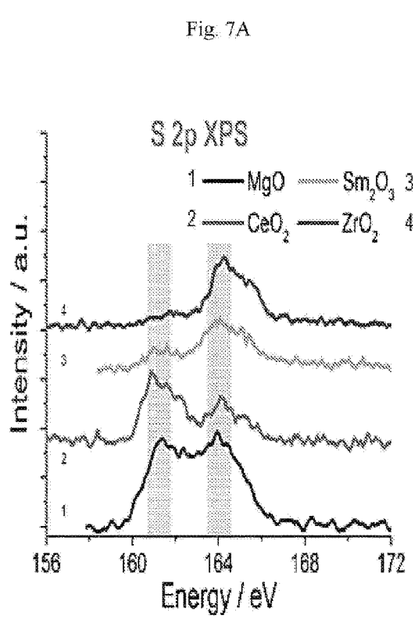
FIGS. 7A-B. (A) S 2p and (B) O 1s spectra of the Mg, Sm, Ce and Zr chalcogenides after OCM at the conditions described herein.

3. X-Ray Absorption Spectroscopy. X-ray photoelectron spectroscopy (XPS) experiments were conducted using Thermo Scientific ESCALAB 250Xi equipped with an electron flood gun and a scanning ion gun, and using Al K$_\alpha$ radiation (1486.6 eV) as the excitation source. After background subtraction, the XPS features were modelled with convoluted Gaussian and Laurenzian functions, taking into account Spin Orbit coupling. From the modelled peaks, the binding energies of the different features were extracted. Based on the relative elemental sensitivities and the C is integrals, the C surface content of the Mg, Zr, Ce and Sm catalysts after reaction is >90%. FIG. 7A shows the S 2p spectra of these catalysts, which are quite similar. Peaks at 161 eV-161.5 eV and at ≈164 eV can be distinguished. Based on earlier studies, the feature at 161 eV-161.5 eV is assigned to a sulfide species, the doublet at 164 eV may be assigned to S$_n$, C—S—C or C—S—H.

Figure 7B:
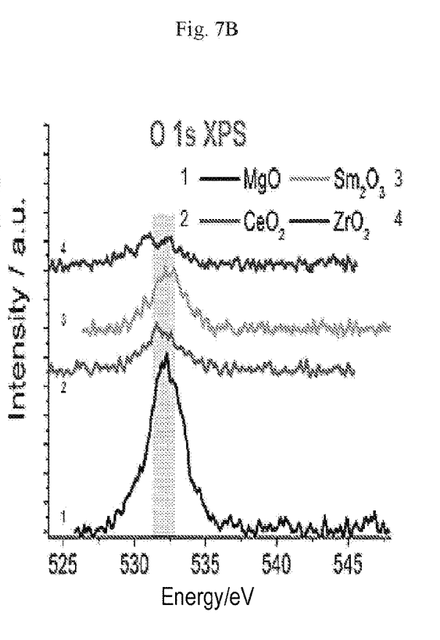
Figure 8:
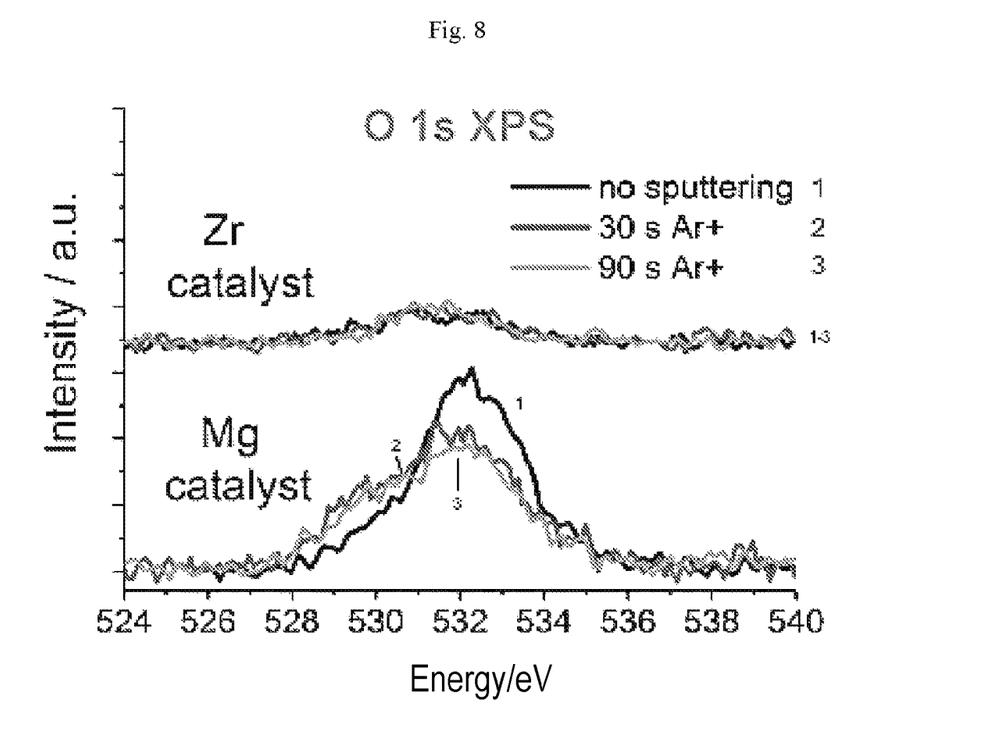
FIG. 8. O 1s spectra of the Mg, and Zr chalcogenides after OCM at the conditions described herein after (1) no sputtering, (2) sputtering with Ar+ ions of an energy of 30 keV for 30 s, and (3) sputtering with $Ar^+$ ions of an energy of 30 keV for 90 s.

The O 1s spectra in FIG. 7B show a weak feature at ≈532 eV and in the case of MgO a small shoulder at 529.7 eV. As only a weak oxide feature can be distinguished for the Mg catalyst, no surface oxides are present on the oxides of Zr, Ce and Sm after reaction. The feature at ≈532 eV may be assigned either to surface O—H, formed during exposure of the catalyst to the atmosphere or to C—O—C species formed on coke. XPS spectra have been collected after sputtering with Ar$^+$ ions with energy 30 keV for 30 s and 90 s in order distinguish between OH groups formed on the immediate surface and C—O—C species which may be present also in the subsurface region. Secondly, these experiments may show whether oxides are present beneath the coke layer. FIG. 8 shows XPS spectra in the 0 1 s region for the Mg and Zr catalysts before and after sputtering for 30 s and 90 s. For both chalcogenides, the peak intensity at 532 eV does not drastically decay, which strongly suggests the presence of a C—O—C species in addition to possible surface M-OH. In the O 1s spectra of Zr and also for Ce and Sm (not shown) after sputtering, no significant increase of a feature at 530 eV can be observed, whereas a slight increase of such a feature is observed on the Mg catalyst. Accordingly, no significant amounts of oxides are present beneath the coke layer.

Figure 9A:
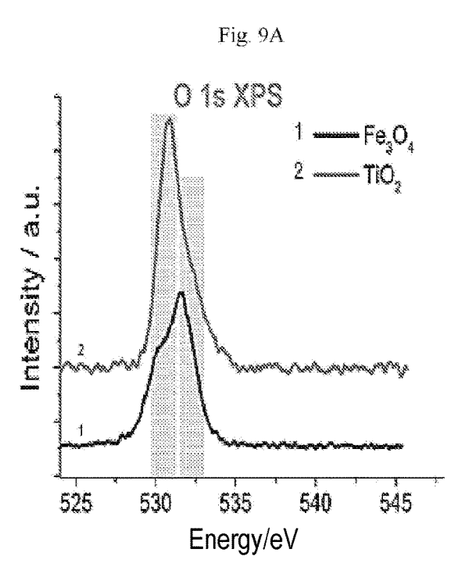
FIGS. 9A-B. O 1s and S 2p spectra of the Ce, Fe and Ti chalcogenides (FIGS. 9A and 9B, respectively) after exposure to the $CH_4/S_2/H_2S/Ar$ mixture at 950° C. for 16 hours.

Based on the relative elemental sensitivities and the C is integrals, the C surface content of the Fe and Ti catalysts after reaction is 12-15%. FIG. 9A shows the O 1s XPS spectra, which show features at ≈530.1 eV and 531-532 eV. The former feature arises from metal oxides whereas the latter feature is assigned to surface hydroxides as its intensity decays significantly after sputtering for 30 s with Ar$^+$ ions of an energy 30 keV. For both chalcogenides, a feature at 161-161.7 can be assigned to metal sulfides containing S$^{2-}$ and possibly a smaller amount of S$_2^{2-}$.

Figure 9B:
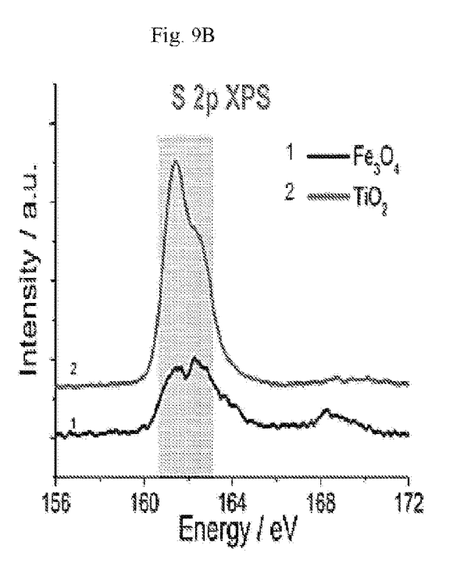

The peak at 168.1 eV, which appears in the S 2p spectrum of the Fe catalyst, results from the presence of SO$_4^{2-}$ on the surface. (FIG. 9B) Note that the peak at 168.1 eV is completely suppressed after sputtering for 30 s, accordingly, SO$_4^{2-}$ is only present on the catalyst surface.

As demonstrated above, OCM processes over metal oxides can be used with S$_2$ as the oxidant. Substantially greater C$_2$H$_4$ selectivities are found versus previous SOMC work, including supported Pd catalysts, and significantly higher C$_2$H$_4$/C$_2$H$_6$ ratios are achieved than previously reported for the OCM with O$_2$. Although the Mg, Zr, W and Sm chalcogenides form significant amounts of coke during SOMC, whereas only minor coking takes place over Fe-, Ti- and Cr-based catalysts, no obvious deactivation of the former catalysts is observed over 16 hours on stream. The enhanced C$_2$H$_4$ yields on the Ce- and Fe chalcogenides suggest that some degree of coking resistance may be necessary to achieve optimum CH$_4$ conversion to C$_2$H$_4$ products. The relative C$_2$H$_6$, C$_2$H$_4$, and C$_2$H$_2$ selectivities as a function of the contact time suggests that the majority of $C_2H_4$ and $C_2H_2$ may be formed via dehydrogenation of $C_2H_6$ and $C_2H_4$, respectively.

We claim:

1. A method for oxidatively coupling methane, said method comprising:
   providing a metal oxide component;
   exposing said metal oxide component to gaseous $S_2$ in the absence of methane for a time and at a temperature sufficient for at least partial sulfidation of said metal oxide component to produce an at least partially sulfidated metal oxide component; and
   contacting said at least partially sulfidated metal oxide component with methane at a methane flow rate and for a time sufficient to oxidatively couple said methane and produce ethylene.

2. The method of claim 1 wherein said metal oxide component is selected from the group consisting of MgO, $ZrO_2$, $TiO_2$, $CeO_2$, $Sm_2O_3$, ZnO, $WO_3$, $Cr_2O_3$, $La_2O_3$, and $Fe_3O_4$.

3. The method of claim 1 wherein each of said gaseous $S_2$ and methane is carried with Ar.

4. The method of claim 1 wherein $H_2S$ is contacted with said at least partially sulfidated metal oxide component.

5. The method of claim 1 wherein ethylene is selectively produced over ethane and acetylene.

6. A method for oxidatively coupling methane, said method comprising:
   providing a metal oxide component selected from the group consisting of MgO, $ZrO_2$, $TiO_2$, $CeO_2$, $Sm_2O_3$, ZnO, $WO_3$, $Cr_2O_3$, $La_2O_3$, and $Fe_3O_4$;
   exposing said metal oxide component to gaseous $S_2$ in the absence of methane for a time and at a temperature sufficient for at least partial sulfidation of said metal oxide component to produce an at least partially sulfidated metal oxide component; and
   contacting said at least partially sulfidated metal oxide component with methane at a methane flow rate and for a time sufficient to oxidatively couple said methane and selectively produce ethylene over ethane and acetylene.

7. The method of claim 6 wherein each of said gaseous $S_2$ and methane is carried with Ar.

8. The method of claim 6 wherein $H_2S$ is contacted with said at least partially sulfidated metal oxide component.

9. The method of claim 6 wherein coke deposits are formed on said at least partially sulfidated metal oxide component during said contacting said at least partially sulfidated metal oxide component with methane.

10. The method of claim 6 wherein said oxidative coupling of methane further produces ethane and wherein increasing said contact time increases the ethylene/ethane molar ratio.

11. A method of using a metal oxide catalyst to oxidatively couple methane, said method comprising:
    providing a metal oxide catalyst component absent the presence of a noble metal;
    exposing said metal oxide catalyst component to gaseous $S_2$ in the absence of methane for a time and at a temperature sufficient for at least partial sulfidation of said metal oxide catalyst component to produce an at least partially sulfidated metal oxide catalyst component; and
    contacting said at least partially sulfidated metal oxide catalyst component with methane at a methane flow rate and for a time sufficient to oxidatively couple said methane and produce ethylene.

12. The method of claim 11 wherein each of said gaseous $S_2$ and methane is carried with Ar.

13. The method of claim 11 wherein $H_2S$ is contacted with said at least partially sulfidated metal oxide catalyst component.

14. The method of claim 11 wherein coke deposits are formed on said at least partially sulfidated metal oxide catalyst component during said contacting said at least partially sulfidated metal oxide catalyst component with methane.

15. The method of claim 11 wherein said oxidative coupling of methane further produces ethane and wherein increasing said contact time increases the ethylene/ethane molar ratio.

16. The method of claim 11 wherein said metal oxide catalyst component is selected from the group consisting of MgO, $ZrO_2$, $TiO_2$, $CeO_2$, $Sm_2O_3$, ZnO, $WO_3$, $Cr_2O_3$, $La_2O_3$, and $Fe_3O_4$.

17. The method of claim 15 wherein said metal oxide catalyst component is a particulate with a diameter of about 180 μm to about 300 μm.

18. A method for oxidatively coupling methane, said method comprising:
    providing a metal oxide component selected from the group consisting of $TiO_2$, $CeO_2$, ZnO, $WO_3$, $Cr_2O_3$, $La_2O_3$, and $Fe_3O_4$;
    exposing said metal oxide component to gaseous $S_2$ for a time and at a temperature sufficient for at least partial sulfidation of said metal oxide component to produce an at least partially sulfidated metal oxide component; and
    contacting said at least partially sulfidated metal oxide component with methane at a methane flow rate and for a time sufficient to oxidatively couple said methane and produce ethylene.

19. The method of claim 18, wherein the metal oxide component is $Fe_3O_4$.

20. The method of claim 18, wherein the metal oxide component is $CeO_2$.

* * * * *